United States Patent [19]

Duic

[11] Patent Number: 5,827,746
[45] Date of Patent: Oct. 27, 1998

[54] METHOD TO DETERMINE THE SEDIMENTATION OF BLOOD AND RELATIVE DEVICE

[75] Inventor: Giovanni Battista Duic, Pavia di Udine, Italy

[73] Assignee: Sire Analytical Systems Srl, Udine, Italy

[21] Appl. No.: 613,233

[22] Filed: Mar. 8, 1996

[30] Foreign Application Priority Data

Mar. 15, 1995 [IT] Italy .................................. UD95A0042

[51] Int. Cl.⁶ .................................................. G01N 33/86
[52] U.S. Cl. .......................... 436/70; 436/164; 436/165; 422/73; 422/82.05; 422/82.09; 356/39; 73/61.65; 73/61.66; 73/61.68; 73/61.69
[58] Field of Search .............................. 436/63, 70, 164, 436/165; 422/68.1, 73, 82.05, 82.09; 435/2, 288.7, 808; 356/39; 73/61.63, 61.64, 61.65, 61.66, 61.68, 61.69

[56] References Cited

U.S. PATENT DOCUMENTS

| | | | |
|---|---|---|---|
| 3,679,367 | 7/1972 | Negersmith et al. | 422/72 |
| 3,684,450 | 8/1972 | Adler et al. | 436/45 |
| 4,041,502 | 8/1977 | Williams et al. | 346/33 A |
| 4,118,974 | 10/1978 | Nozaki et al. | 73/61.69 |
| 4,135,819 | 1/1979 | Schmid-Schönbein | 356/39 |
| 4,352,557 | 10/1982 | Schmid-Schonbein | 356/39 |
| 4,566,315 | 1/1986 | O'Brien et al. | 73/61.69 |
| 4,822,568 | 4/1989 | Tomita | 422/73 |
| 4,848,900 | 7/1989 | Kuo et al. | 356/39 |
| 5,003,488 | 3/1991 | Hardy | 364/509 |
| 5,316,729 | 5/1994 | Orth et al. | 422/73 |
| 5,328,822 | 7/1994 | McKinney et al. | 435/4 |
| 5,567,869 | 10/1996 | Hauch et al. | 73/64.41 |

FOREIGN PATENT DOCUMENTS

| | | |
|---|---|---|
| 9216127 | 4/1994 | Denmark . |
| 92/09879 | 6/1992 | WIPO . |
| 94/18557 | 8/1994 | WIPO . |

*Primary Examiner*—Maureen M. Wallenhorst
*Attorney, Agent, or Firm*—Antonelli, Terry, Stout & Kraus, LLP

[57] ABSTRACT

Method and apparatus to determine the sedimentation of blood. A blood sample is taken, and an anti-coagulant substance is added. The sample is homogenized. The method includes a step of measuring an optical density, or absorbance, of the sample as a function of time and without waiting for the formation of a plasma/corpuscle interface to obtain an optical density measurement. The measurements are carried out at any fixed point of a reading container which contains a micro-volume of blood. The inner diameter of the containing chamber ensures a linear relationship between the optical density and the number of corpuscles present. Finally, the optical density measurement is processed to obtain a speed of sedimentation.

26 Claims, 1 Drawing Sheet

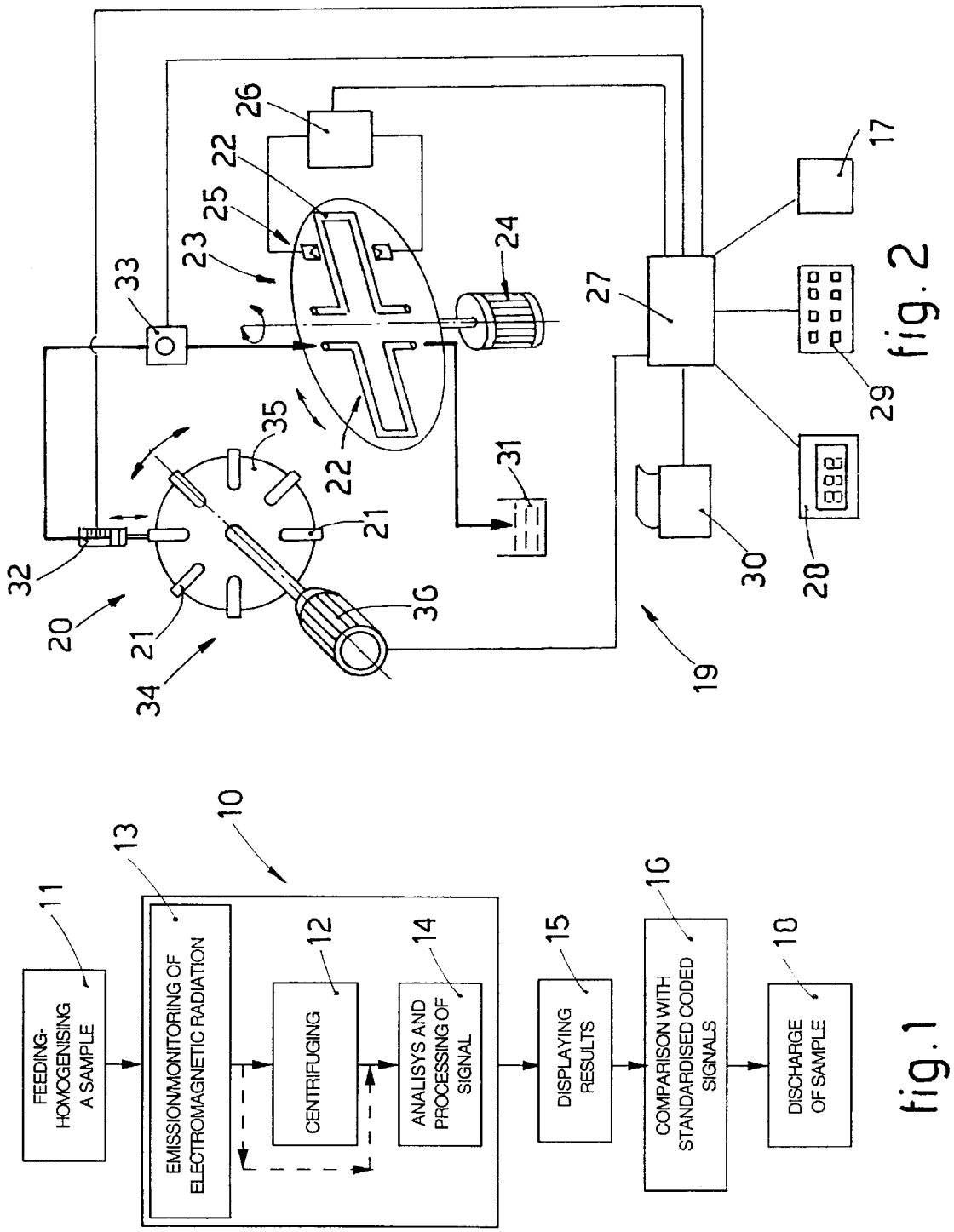

1

METHOD TO DETERMINE THE SEDIMENTATION OF BLOOD AND RELATIVE DEVICE

FIELD OF INVENTION

This invention concerns a method to determine the sedimentation of blood and the relative device, as set forth in the respective main claims.

The invention is applied to the field of medical analyses and enables the speed of sedimentation of blood to be determined quickly and automatically.

BACKGROUND OF THE INVENTION

It is well known that the measurement of the speed of sedimentation of the part of the blood containing corpuscles and, to be more exact, of the erythrocytes is linked in some way to the state of health of the patient.

This speed of sedimentation is called in the technical field VES (velocity of erythrocyte sedimentation) or ESR (erythrocyte sedimentation rate), these terms being employed for the sake of simplicity in the description that follows.

The sedimentation of the red corpuscles in the blood takes place in three phases as follows:
- a first phase of aggregation of the red corpuscles due to electrostatic forces and to the content of some proteins in the plasma; this aggregation leads to the formation of rouleaux of various dimensions according to the parameters cited; this first phase lasts for about 1 to 10 seconds;
- a second phase of sedimentation of the rouleaux; this value expresses various characteristics according to the pathologies possibly present; this phase, under the action of the force of gravity alone, may last for some tens of minutes up to hours;
- a third phase of final packing of the rouleaux; these rouleaux tend to arrange themselves by taking up all the available volume on the basis of the difference of density between the rouleaux and the plasma; this phase, under the action of the force of gravity alone, may last for some tens of minutes up to hours.

The parameter which is usually considered in the measurement of the VES is the second one above, although the first is intimately interconnected with the VES.

It is known in particular that during the pathological conditions defined as inflammatory the VES increases and therefore this analysis is used to ascertain the presence of such pathological conditions in a quick and easy manner.

Many different systems have been used hitherto to measure this speed of sedimentation.

In a classic system the sample of blood drawn from the patient into suitable containers holding anti-coagulant substances is distributed into suitable tubes, or test tubes, which are generally positioned vertically on appropriate supports.

The analysis consists in observing at pre-set fixed times the position of the band of separation, or interface, between the fluid plasma part of the blood, which is clear, and the part containing corpuscles, which consists of erythrocytes, leukocytes and blood platelets, which is red.

The data measured give the speed of sedimentation of the blood.

This method, however, is slow and not automatic and errors may easily be made by the laboratory assistant in the reading and/or transcription of the data giving the height of the interface.

Various systems to overcome these shortcomings have been disclosed so as to obtain such analysis in an automatic, fast and reproduceable manner.

CH-A-655.800 discloses a method of monitoring, at pre-set intervals of time, the light transmitted through the sedimentation tube so as to identify the position of the plasma/corpuscles interface. This system enables the analysis to be automated but does not reduce the performance times.

GB-A-2,153,072 discloses a method whereby the measurement tubes are inclined to the vertical and are then caused to rotate so as to exploit centrifugal force in accelerating the sedimentation of the erythrocytes and are lastly uprighted to a vertical position to perform the reading of the position of the plasma/corpuscles interface. This system enables the times for carrying out the analysis to be indeed reduced but in a manner not satisfactory enough for users.

DE-A-2.825.659 discloses the reading of the optical density of the blood along a determined segment of the sedimentation tube by using a plurality of vertically arranged diodes. This measurement provides the variation in time of the position of the plasma/corpuscles interface and therefore the VES.

U.S. Pat. No. 4,848,900 discloses a device to evaluate the optical density at the plasma/corpuscles interface; by moving the movable reading head step-by-step and automatically it is possible to obtain the VES of the analysed sample of blood.

U.S. Pat. No. 5,003,488 discloses the use of a telecamera to identify the height of the interface at determined intervals and to process with a computer the data thus measured so as to obtain the VES.

U.S. Pat. No. 5,316,729 discloses a device to monitor by analysis of the optical density the movement of the plasma/corpuscles interface and to compare the curve thus obtained with reference curves so as to extrapolate the final position of that interface and to determine the VES.

WO 91/05996 discloses a device whereby the VES is monitored by opto-thermal sensors which measure at determined intervals the heat produced by the absorption, by the sample itself, of radiation which strikes the sample of blood to be analysed. The signals monitored at determined intervals of time are a function of the VES of the sample U.S. Pat. No. 5,328,822 discloses a method and a device whereby the position of the plasma/corpuscles interface is monitored by an analysis of reflectivity of the light on the tube being analysed, this characteristic being a function of the number of corpuscles present corresponding to the sensor.

This device provides for the use of a step motor associated with the movable reading head, which is lowered along the tube and determines by extrapolation the exact position of the plasma/corpuscles interface. Moreover, this document provides also for the diagnosis of the pathology of the patient by comparing the curve obtained with sample curves and also provides for the analysis of the curve of sedimentation of the part containing corpuscles and of the plasma, including leukocytes and blood platelets after sedimentation of the erythrocytes.

U.S. Pat. No. 3,824,841 and U.S. Pat. No. 3,848,796 disclose a method and a device whereby the analysis tubes containing the blood are kept vertically and set in rotation, still in a vertical position, until those tubes are subjected to a centrifugal acceleration equal to 6 to 8.5 times the acceleration of gravity.

The level reached by the plasma/corpuscles interface is read at determined intervals of time after one or more cycles of centrifuging so as to obtain the measurement of the VES.

All the methods disclosed so far, some of which have been briefly set forth, enable the performance of the analysis to be automated but do not enable the performance times to be reduced except very slightly.

Moreover, all these methods require that the blood to be analysed should be contained in appropriate containers of the disposable type with a resulting increase in the costs of the analysis as regards both the purchase and, above all, the disposal of these containers, which have to be treated as hospital refuse.

Moreover, the quantity of blood required for performing the analysis is great and is such as will create problems in some cases, particularly when the analysis has to be carried out on children.

Furthermore, all the methods disclosed hitherto are based on the monitoring in time of the position of the plasma/corpuscles interface, which is determined gradually as the particles of blood settle.

This type of monitoring requires of necessity a minimum performance time, even if it is greatly reduced by submitting the vertically kept container to centrifuging about a vertical axis so as to accelerate the sedimentation of the particles.

In fact, the monitoring system entails an initial dead time which cannot be eliminated and in which the formation of the plasma/corpuscles interface has to take place.

At the present time it is therefore not possible to combine in parallel the device performing this analysis with other existing devices able to carry out other very fast analyses such as the haemochromocytometric analysis, in which is carried out the counting of the number of the erythrocytes, leukocytes and blood platelets.

Moreover, the devices of the state of the art require the use of a container intended for this type of analysis and of a specially intended device, this situation being a possible source of errors due to the exchange of samples or to wrong labelling if the various analyses are performed with different instruments and also in different times.

The times of performance of the analysis of the VES with the devices of the state of the art are always greater than 90 seconds and generally greater than 120 seconds, whereas the haemochromocytometric analysis cited above has performance times less than a minute.

U.S. Pat. No. 3,679,367 and U.S. Pat. No. 3,684,450 disclose a method and relative device for determining the haematocrit or the volume of packed red corpuscles by using very high speeds of rotation to ensure a swift packing of the corpuscles.

This method therefore refers to the third phase of sedimentation and not to the second in which the methods of sedimentation, and therefore the VES, are analysed.

Moreover, this method determines the volume of packed corpuscles by measuring continuously the position of the interface found from the different optical density between the lymph plasma and the corpuscles.

The present applicants have designed, tested and embodied this invention to overcome the shortcomings of the state of the art and to achieve further advantages.

SUMMARY OF THE INVENTION

This invention is set forth and characterised in the respective main claims, while the dependent claims describe variants of the idea of the main embodiment.

The purpose of this invention is to provide a method For the monitoring of the speed of sedimentation of blood (VES), the method being immediate and secure.

The invention enables the analysis to be performed by using micro-volumes of blood so that the invention can be used without problems also in the field of paediatrics or on anaemic patients.

The invention enables the analysis to be performed by taking the sample to be analysed directly from any container containing blood, to which has been added any anti-coagulant substance but advantageously salts of EDTA (ethylene diamine tetra-acetic acid), and used in laboratories of clinical analyses without having to use specially provided a containers, thus making possible a resulting saving of disposable material and of blood.

The invention obviates the possibility of mistakes due to exchanges of containers between patients inasmuch as the analysis of the VES is carried out at the same time and with the same performance times as other clinical analyses such as the haemochromocytometric examination, as it is possible to use the same sample of blood contained in the test tube for the haemochromocytometric examination too.

The invention makes also possible the immediate identification of other characteristics of the patient such as, for instance, the inclusion of a low number of erythrocytes, these being characteristics which have to be kept in mind for the analysis of the VES so as not to fall into errors of evaluation in correlating the number of corpuscles present with the VES found.

BRIEF DESCRIPTION OF THE FIGURES

FIG. 1 is a block diagram of the method according to the invention;

FIG. 2 is a diagram of a device according to the invention.

DESCRIPTION OF THE INVENTION

The method according to the invention is based on the monitoring of the optical density of the sample of blood with any position of the container employed for the measurement.

In the method according to the invention the width of the sample of blood analysed has to be very small so that the law of Lambert-Beer on absorbance or optical density, can be applied.

The law of Lambert-Beer establishes that:

$$A = k.c.d$$

where:

A=absorbance or optical density defined as: $\log (I_0/I)$ with $I_0$=intensity of the luminous radiation which passes through the empty container and I=intensity of the luminous radiation which passes through the container filled with the sample to be analysed;

c=concentration of the species which absorbs the radiation;

d=width of the sample thus passed through;

k=constant.

In this case the signal monitored is therefore directly in proportion to the number of corpuscles contained in the sample at that point and thus gives an immediate indication without initial dead times since it is not necessary to await the formation of the plasma/corpuscles interface as in the state of the art.

Over a period of time the number of corpuscles present at the point of observation changes owing to the fact that the corpuscles tend to settle, and this variation changes the value of the absorbance at that point.

Therefore, the study of the absorbance over a period of time is equivalent to the study of the corpuscles present at that point over a period of time and thus can be correlated with the VES.

The observation point can be located either in the initial part, where the number of corpuscles diminishes over a period of time, or in the final part of the container, where the number of corpuscles increases over a period of time.

By initial part and final part of the container are meant the parts positioned in the vicinity of, and distanced from, the axis of rotation respectively.

Depending on whether the observation point is located in the initial part or final part of the container, the absorbance decreases over a period of time or increase over a period of time.

The method according to the invention comprises the following steps:

the feeding of the sample of suitably homogenised blood to the analysis device, for instance, by aspiration from the container holding the blood drawn;

the possible centrifuging of the sample in the container of a small inner diameter of between 0.1 and 2.0 mm, such as a capillary tube; this centrifuging step is advantageously carried out about an axis perpendicular to the plane of positioning of the container; the speed of centrifuging used to optimise the step of sedimentation of the rouleaux is such as to submit the sample of blood to an acceleration between 2 and 20 g, but advantageously between 7 to 8 g;

the monitoring as a function of time of the optical density of the sample at any fixed and determined point in the container; this monitoring can be carried out advantageously by using electromagnetic radiations having a wave length between 200 and 1000 nm, but advantageously between 700 and 1000 nm;

processing of the signal obtained over a period of time and conversion of the parameters of the curve which plots the optical density as a function of time so as to determine the VES, with a possibility of making a graph of the total sedimentation; according to whether the point of observation is located in the initial part or final part of the sample, the curve obtained will have a decreasing or increasing development as a function of time;

comparison with standardised coded signals;

discharge of the sample.

The method according to the invention can be employed also to monitor analytically and quantitatively the sedimentation of the plasma part of the blood.

The method according to the invention can be combined with other methods to carry out other analyses which use containers containing blood to which an anti-coagulant has been added and which have very short performance times such as a haemochromocytometric examination for instance.

The device according to the invention comprises means to draw the sample to be analysed from the drawing container and also means to centrifuge the sample, these latter means being associated with an assembly which emits/monitors electromagnetic radiation for monitoring the optical density of the sample at a fixed and determined point.

In the device according to the invention the sample is delivered into a container which is rotated about an axis perpendicular to the plane of positioning of the container with a determined angular velocity which can be varied as required as a function of the desired duration of the analysis.

This container is made of a material transparent to the electromagnetic radiation employed by the assembly used to monitor the optical density.

According to a particular form of embodiment of the device according to the invention this container has a through passage and includes an inlet and an outlet to make possible access to the sample to be analysed and the downflow and discharge of the sample when the analysis has been completed.

According to a particular formulation of the invention the container of the sample to be analysed consists of a capillary tube which extends without a break of continuity from the point of receipt of the sample to the discharge point.

This formulation is especially advantageous inasmuch as it prevents contact of the sample of blood with the atmosphere, thus obviating possible pollution and loss of the sample.

Moreover, this solution makes possible the flushing of the whole container between one examination and another with a suitable washing solution to prevent contagion between various samples of blood.

The assembly which emits/monitors the electromagnetic radiation is positioned perpendicular, or substantially perpendicular to the plane of positioning of the container and on opposite sides of the container and remains positioned at a fixed determined point during the performance of the analysis.

According to a variant the assembly emitting/monitoring the electromagnetic radiation can be positioned radially as desired.

According to a further variant the container has a reflecting sidewall and the emitting/monitoring assembly is positioned on one and the same side of the plane of positioning of the container.

As we said above, the emitting/monitoring assembly can be positioned either at the initial part of the container nearest to the axis of rotation, where the optical density diminishes over a period of time, or at the final part of the container distanced from the axis of rotation, where the optical density increases over a period of time.

The device according to the invention is advantageously governed by a programming, processing and control assembly, which controls all the steps of the analysis such as the aspiration of the sample, the centrifuging of the sample, the monitoring of the optical density of the sample at determined intervals, the processing of the signal monitored over a period of time and the discharge of the sample.

Moreover, the programming, processing and control assembly is associated with means that represent the signal either on a video or on a printer.

According to a variant, the programming, processing and control assembly comprises a bank of reference data, for instance in the form of curves or tables with which are compared the monitored signals so as to diagnose possible pathologies.

According to a variant the device according to the invention is combined with a supply store holding a plurality of samples of blood to which anti-coagulant substances have been added; these samples of blood are suitably homogenised, for instance by rotation, rocking or other analogous operations.

This supply store positions in sequence each sample from which a micro-volume of blood to form the sample to be analysed is aspirated in an automatic manner, for instance by means of a needle.

According to a further variant the container is automatically re-sealed after the aspiration step so as to prevent possible contamination.

The attached figures are given as a non-restrictive example and show a preferred embodiment of the invention as follows:

The reference number 10 in the attached figures denotes generally a method to determine the sedimentation of blood (VES) according to the invention.

The method 10 according to the invention includes the following steps:

feeding 11 the suitable homogenised sample to be analysed, for instance by aspiration from a container 21 into a reading container 22 defining a containing chamber having a very small inner diameter, into which is inserted the micro-volume of sample to be analysed;

possible centrifuging 12 of the sample about an axis substantially perpendicular to the plane of positioning of the reading container 22; the speed of centrifuging used to optimise the step of sedimentation of the rouleaux is such as to subject the sample of blood to an acceleration between 2 and 20 g, but advantageously between 7 to 8 g;

emission/monitoring 13 of an electromagnetic radiation to identify the development over a period of time of the optical density of the sample of blood analysed at any fixed point of the reading container 22, this emission/monitoring 13 being carried out in a direction perpendicular to the plane of positioning of the reading container 22 containing the sample and with a momentary scanning which can be programmed as desired immediately after the first moment at which the sample is injected into the reading container 22, the minimum usable duration of emission/monitoring 13 being selected as a function of the speed of centrifuging;

the analysis and processing 14 of the monitored signals as a function of the period o time, taking into consideration the initial value of the absorbance which is a function of the number of corpuscles present in the sample analysed;

display 15 of the results by video 28 and/or on a printer 30;

possible comparison 16 with standardised signals of coded pathologies;

discharge 18 of the analysed sample.

The method 10 according to the invention is very quick and accurate and makes possible the reading over a period of time of the optical density of the sample so as to describe in a quantitative analytical manner all the steps of the sedimentation which can be used to identify various inflammatory pathologies.

The use of reading or capillary containers 22 defining a containing chamber of a small inner diameter for the reading of the optical density of a sample of blood enables a linear response to be obtained between the optical density and the quantity of corpuscular mass contained in the blood being examined, this situation enabling results regarding the VES to be provided inasmuch as the optical density at any point of the reading container 22 is a function of the number of corpuscles contained in the sample being examined at every moment during the centrifuging.

The reading container 22 defines a containing chamber having an inner diameter between 0.1 mm. and 2 mm., but advantageously 1 mm.

The reference number 19 indicates generally a particular form of embodiment of a device suitable to perform the above method 10.

In this case the device 19 comprises:

an aspiration system 20 to aspirate a micro-volume of blood from a container 21;

a capillary reading container 22 lying on a substantially horizontal plane and associated with centrifuging means 23, which consist in this case of a first motor 24 having a vertical axis;

an assembly 25 to emit/monitor electromagnetic radiations which is positioned perpendicular to, and on opposite sides of, the plane of positioning of the capillary reading container 22;

a means 26 to acquire the signal monitored by the monitoring assembly 25;

a programming, processing and control assembly 27 which governs automatically the device 19 performing the method and which comprises display means 28, means 29 to introduce data and control and printing means 30;

a means 31 to discharge the analysed sample.

According to a variant a means is also included to flush a suitable solution for washing and sterilising the reading container 22 between one analysis and the next one.

According to a particular formulation of the invention, which is not shown here, the container 22 of the sample to be analysed consists of a capillary tube which extends without a break of continuity from the point of receipt of the sample to the discharge point.

This formulation is especially advantageous since it prevents contact of the sample of blood with the atmosphere, thus obviating possible pollution and loss of the sample.

The programming, processing and control assembly 27 enables all the methods of performing the analysis to be programmed as desired, such as the speed and cycle of the centrifuging of the sample, the momentary scanning of the emitting/monitoring assembly 25 and the representation of the results.

In this case the aspiration system 20 comprises syringe means 32 and pump means 33, and the sample-drawing container 21 is associated with a sample storage assembly 34 consisting of a rotary drum 35 driven by a second motor 36 and including on its periphery a plurality of sample-drawing containers 21.

This rotary drum 35 is halted advantageously at a position suitable for the drawing of a micro-volume of sample by means of the syringe means 32.

According to a particular form of embodiment the syringe means 32 are associated with a sealing assembly which closes the hole made in the stopper of the container 21 by the needle of the syringe means 32.

According to a particular form of embodiment the device 19 according to the invention is associated with other apparatuses for the performance of examinations, such as the haemochromocytometric examination for instance, these apparatuses being fed advantageously by the same aspiration system 20 and being governed by the same programming, processing and control assembly 27.

It is possible in this way to combine the result of the VES examination with other examinations carried out at the same time on a sample of blood drawn from the same container 21.

In an advantageous form of embodiment of the device 19 according to the invention the assembly 25 emitting/monitoring electromagnetic radiations can be positioned radially in any usable radial position of the capillary reading container 22.

According to a variant the programming, processing and control assembly 27 comprises a bank of reference data 17 containing, for instance in the forms of curves or tables, characteristic signals with which are compared the signals monitored by the device 19 according to the invention so as to diagnose possible pathologies.

I claim:

1. Method to determine the speed of sedimentation of corpuscles present in a sample of blood, the method being carried out on a sample consisting of blood to which any anti-coagulant substance has been added and which is suitably homogenized, the method comprising the steps of measuring an optical density, or absorbance, of a homogenized sample of blood to which an anticoagulant has been added, as a function of time and without waiting for the formation of a plasma/corpuscle interface to obtain an optical density measurement, the measuring step being carried out at any fixed point of a reading container defining a containing chamber of an inner diameter of between 0.1 and 2.0 mm which contains a micro-volume of the sample of blood, the inner diameter of the containing chamber ensuring a linear relationship between the optical density and the number of corpuscles present in the sample of blood, and wherein the reading container is subjected to centrifuging during the measuring step; and processing said optical density measurement to obtain a speed of sedimentation of corpuscles in the blood sample.

2. Method as in claim 1, wherein said method enables a value of a corpuscular mass in the sample of blood to be identified.

3. Method as in claim 1, in which during the centrifuging the sample undergoes an acceleration between 2 and 20 g.

4. Method as in claim 3, in which the centrifuging takes place about an axis perpendicular to a plane of positioning of the reading container.

5. Method as in claim 3, in which during the centrifuging the sample of blood undergoes an acceleration of between 7 to 8 g.

6. Method as in claim 1, which is independent of the type of anti-coagulant substance added to the sample of blood.

7. Method as in claim 1, wherein said method is governed by a programming, processing and control assembly for an automatic determination of the speed of sedimentation.

8. Method as in claim 1, wherein said method enables the sedimentation of a plasma part of the sample of blood to be measured in an analytical and quantitative manner.

9. Method to determine the speed of sedimentation of corpuscles present in a sample of blood, the method being carried out on a sample of blood to which an anti-coagulant has been added, comprising the steps of:

homogenizing and adding an anti-coagulant to a sample of blood and feeding the sample of blood to be analyzed into a reading container;

centrifuging the sample of blood about an axis perpendicular to a plane of positioning of the reading container;

emitting and monitoring an electromagnetic radiation at a fixed point of the reading container holding the blood sample, while centrifuging to measure development, over a period of time, of an optical density of the sample of blood analyzed without waiting for the formation of a plasma/corpuscle interface to obtain the optical density measurement;

processing optical density signals as a function of a period of time;

displaying speed of sedimentation results obtained from the processed optical density signals; and discharging the analyzed sample of blood from the reading container.

10. Method as in claim 9, which further comprises a step of comparison of optical density signals with previously stored measurements associated with known pathologies, wherein said step of comparison is used to determine inflammatory pathologies.

11. Device for determining the speed of sedimentation of corpuscles in blood, comprising, at least one means for feeding a homogenized sample of blood to which an anticoagulant has been added to a reading container set in rotation about an axis perpendicular to a plane of positioning of the reading container by a means for centrifuging, an emitting and monitoring assembly to emit and monitor electromagnetic radiations, wherein said assembly is positioned at a fixed point perpendicular to a plane of positioning of the reading container, a means for acquiring optical density data and a programming, processing and control assembly; wherein the reading container defines a containing chamber having an inner diameter between 0.1 and 2 mm and wherein optical density data measurements are acquired without waiting for a plasma/corpuscle interface to form in the sample of blood.

12. Device as in claim 11, in which the reading container comprises an inlet and an outlet for feeding and discharge of the sample of blood.

13. Device as in claim 11, in which the reading container extends, without a break of continuity, from a feed to a discharge of the sample of blood.

14. Device as in claim 11, in which the emitting and monitoring assembly and the means to acquire optical density data enables the development, over a period of time, of the optical density of the sample of blood, wherein said development over time is correlated with the speed of sedimentation (VES).

15. Device as in claim 11, in which the emitting and monitoring assembly is positioned as desired along an axis of the reading container.

16. Device as in claim 11, in which the reading container has a reflecting surface, and the emitting and monitoring assembly has emitting means and monitoring means positioned on a same side of the plane of positioning of the reading container.

17. Device as in claim 11, in which the rotation about an axis perpendicular to the plane of positioning of the reading container by the means for centrifuging is performed by a centrifuge and the centrifuge can be adjusted as desired as a function of a desired duration of analysis.

18. The device of claim 17, wherein a gradient of acceleration and a final value of acceleration can be adjusted in said centrifuge.

19. Device as in claim 11, which subjects the sample of blood to a centrifugal acceleration of between 2 and 20 g.

20. Device as in claim 19, which subjects the sample of blood to a centrifugal acceleration of between 7 to 8 g.

21. Device as in claim 11, in which, the emitting and monitoring assembly and the means to acquire optical density data can be adjusted as desired.

22. Device as in claim 11, in which the programming, processing and control assembly is associated with a bank of reference data.

23. Device as in claim 11, wherein said device is further coupled hydraulically and electronically to other apparatuses for performance of other analyses of blood.

24. Device as in claim 23, wherein the other analyses of blood performed is a haemochromocytometric examination.

25. Device as in claim 11, further comprising a means to flush a suitable solution for washing and sterilization of the reading container between one analysis and a subsequent analysis.

26. The device of claim 11, wherein the reading container defines a containing chamber having an inner diameter of 1 mm.

* * * * *